United States Patent [19]

Harada et al.

[11] Patent Number: 4,486,605

[45] Date of Patent: Dec. 4, 1984

[54] METHOD FOR PRODUCING AROMATIC CARBONYL COMPOUNDS

[75] Inventors: Haruhisa Harada; Hiroshi Maki, both of Chiba, Japan

[73] Assignee: Sumitomo Chemical Company, Limited, Osaka, Japan

[21] Appl. No.: 456,455

[22] Filed: Jan. 7, 1983

[30] Foreign Application Priority Data

Jan. 7, 1982 [JP] Japan ................................. 57-1573
Aug. 12, 1982 [JP] Japan ............................. 57-140658
Oct. 28, 1982 [JP] Japan ............................. 57-190567

[51] Int. Cl.$^3$ ............................................. C07C 45/53
[52] U.S. Cl. ................................. 568/311; 568/335; 568/336; 568/315; 460/51; 460/52; 460/53; 562/459; 562/462; 562/463
[58] Field of Search ................ 568/311, 315, 336, 335; 560/51, 52, 53; 562/459, 462, 463

[56] References Cited

U.S. PATENT DOCUMENTS

| | | | |
|---|---|---|---|
| 2,557,968 | 6/1951 | Hulse et al. | 568/311 |
| 2,671,111 | 3/1954 | Butler | 568/315 |
| 2,993,072 | 7/1961 | Chiusoli et al. | 568/311 |
| 3,161,685 | 12/1964 | Minisci et al. | 568/311 |
| 3,197,488 | 7/1965 | Braunworth et al. | 568/311 |
| 3,671,810 | 3/1954 | Coffman et al. | 568/311 |
| 3,968,162 | 7/1976 | Lartigau et al. | 568/311 |

OTHER PUBLICATIONS

Ogata et al., Chem. Abst., vol. 79, #77781U, (1973).
Kharasch et al., J. Org. Chem., vol. 15, pp. 763–774, (1950).
Boardman, J.A.C.S., vol. 75, pp. 4268–4271, (1971).

*Primary Examiner*—James H. Reamer
*Attorney, Agent, or Firm*—Sughrue, Mion, Zinn, Macpeak and Seas

[57] ABSTRACT

A method for producing an aromatic carbonyl compound represented by the formula (B)-1 or (B)-2:

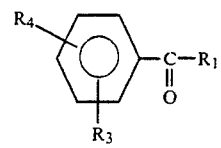

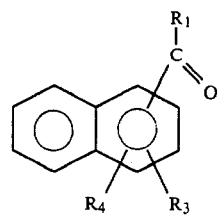

comprising decomposing a hydroperoxide represented by the formula (A)-1 or (A)-2:

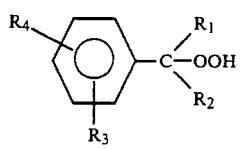

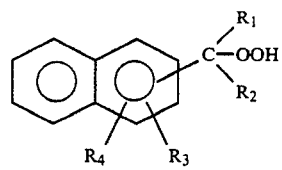

wherein R$_1$, R$_2$, R$_3$ and R$_4$ are defined in the specification, in an inert gas atmosphere in the presence of an aqueous layer containing an iron salt, a copper salt and an acid is disclosed. Novel m-(2-hydroxy-2-propyl)acetophenone and m-isopropenylacetophenone which are useful as an intermediate for the preparation of medicines are also disclosed. A method for producing m-isopropenylacetophenone comprising dehydrating m-(2-hydroxy-2-propyl)acetophenone in the presence of an acid catalyst is further disclosed.

6 Claims, No Drawings

METHOD FOR PRODUCING AROMATIC CARBONYL COMPOUNDS

FIELD OF THE INVENTION

The present invention relates to a method for producing an aromatic carbonyl compound comprising decomposing a hydroperoxide. The present invention also relates to a novel acetophenone derivative.

BACKGROUND OF THE INVENTION

The conventionally well-known methods for synthesizing carbonyl compounds by the decomposition of hydroperoxide are as follows:

(1) A method of decomposition by heating in the coexistence of an aqueous alkali solution.
(2) A method of decomposition with potassium ferrocyanide [J.A.C.S., 75, 4268 (1953)].
(3) A method of decomposition with a ferrous salt ($Fe^{++}$) [J. Org. Chem., 15, 763 (1950), etc.].

By the method (1), however, large quantities of alcohol compounds are produced at the same time, so that carbonyl compounds cannot be obtained in good yields.

The method (2), according to the description of the literature cited, produces acetophenone in very high yield from cumene hydroperoxide, but because of this reaction being almost stoichiometric, a large quantity of expensive potassium ferrocyanide need to be used. Consequently, this method cannot always be said to be industrially advantageous.

The method (3) is described in many studies and literatures from of old, and, for example, according to the description of the literature given above, acetophenone is obtained in a yield of 71% by the decomposition of cumene hydroperoxide with a ferrous salt ($Fe^{++}$). In this method with a ferrous salt ($Fe^{++}$), however, the amount of the salt used is generally large, and the yield is also low, so that this method cannot always be said to be advantageous from the industrial point of view, too.

In view of the present situation like this, the present inventors extensively studied and found that, by decomposing a hydroperoxide in an inert gas atmosphere in the presence of an aqueous layer containing an iron salt, a copper salt and an acid, aromatic carbonyl compounds can be obtained in markedly high yields as well as with a rapid decomposition rate. The present invention was completed based on this finding.

SUMMARY OF THE INVENTION

An object of the present invention is to provide a method for producing an aromatic carbonyl compound represented by the formula (B)-1 or (B)-2:

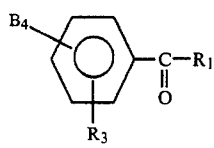

(B)-1 wherein $R_1$ is a hydrogen atom or a methyl group; and $R_3$ and $R_4$ are each a hydrogen atom, a ($C_1$-$C_3$)alkyl group,

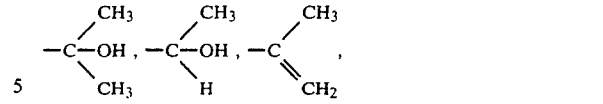

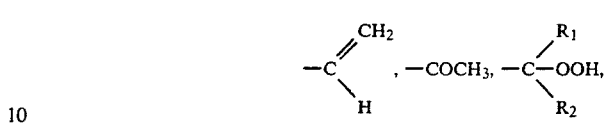

—COOH, or a carboxylic acid ester group,

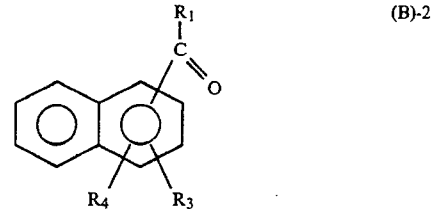

(B)-2 wherein $R_1$, $R_3$ and $R_4$ are the same as defined above, comprising decomposing a hydroperoxide represented by the formula (A)-1 or (A)-2:

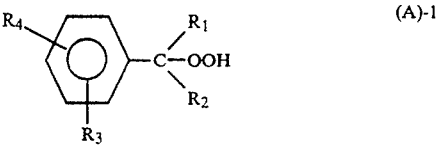

(A)-1 wherein $R_2$ is a hydrogen atom or a methyl group; and $R_1$, $R_3$ and $R_4$ are the same as defined above,

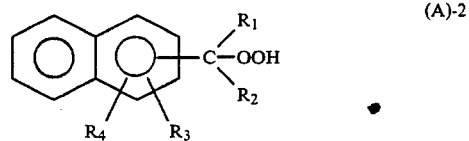

(A)-2 wherein $R_1$, $R_2$, $R_3$ and $R_4$ are the same as defined above, in an inert gas atmosphere in the presence of an aqueous layer containing an iron salt, a copper salt and an acid.

Another object of the present invention is to provide m-(2-hydroxy-2-propyl)acetophenone and m-isopropenylacetophenone, each being included in the scope of the above formula (B)-1.

A further object of the present invention is to provide a method for producing m-isopropenylacetophenone comprising dehydrating m-(2-hydroxy-2-propyl)acetophenone in the presence of an acid catalyst.

DETAILED DESCRIPTION OF THE INVENTION

Specific examples of the hydroperoxide represented by the formula (A)-1 or (A)-2 include cumene hydroperoxide, cymene hydroperoxide, diisopropylbenzene dihydroperoxide, ethylcumene hydroperoxide, diisopropylbenzene monohydroperoxide, diethylbenzene monohydroperoxide, m-(2-hydroxy-2-propyl)cumene hydroperoxide, isopropenylcumene hydroperoxide, ethylbenzene hydroperoxide, (α-hydroxyethyl)ethylbenzene hydroperoxide, acetylcumene hydroperoxide, triisopropylbenzene trihydroperoxide, methyl cuminate hydroperoxide, isopropylnaphthalene hydroperoxide and the like.

Specific examples of the aromatic carbonyl compound represented by the formula (B)-1 or (B)-2 include acetophenone, methylacetophenone, ethylacetophenone, isopropylacetophenone, m-(2-hydroxy-2-propyl)-acetophenone, m-isopropenylacetophenone, (α-hydroxyethyl)-acetophenone, vinylacetophenone, diacetylbenzene, acetylcumene hydroperoxide, triacetylbenzene, methyl acetylbenzoate, acetylnaphthalene and the like. Of these compounds, m-(2-hydroxy-2-propyl)acetophenone and m-isopropenylacetophenone are useful as an intermediate for the preparation of medicines, such as, for example, phenylephrine hydrochloride represented by the formula:

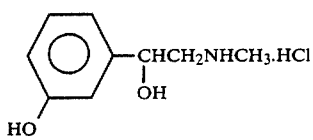

which is known as a vasoconstrictor.

The production of the hydroperoxide represented by the formula (A)-1 or (A)-2 is not particularly limited, but a method generally used in industry is air-oxidation of a compound represented by the formula (C)-1 or (C)-2:

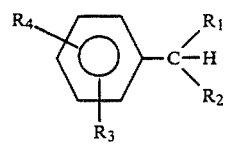 (C)-1

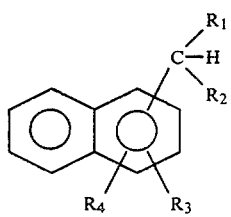 (C)-2 wherein $R_1$, $R_2$, $R_3$ and $R_4$ are the same as defined above. Thus, the hydroperoxide represented by the formula (A)-1 or (A)-2 can be easily obtained.

The hydroperoxide can be used alone or in admixture of two or more thereof.

The method of the present invention is carried out in an inert gas atmosphere such as nitrogen, helium or the like. Under aerial or oxygen atmosphere, the metal salt is oxidized, the reaction rate slows down, and besides the yield of the aromatic carbonyl compound lowers, so that such atmosphere is not desirable.

In the method of the present invention, the coexistence of both an iron salt and a copper salt is essential. The use of an iron salt alone has defects such that: The yield of the aromatic carbonyl compound is low; and the decomposition of the hydroperoxide is very fast at the initial stage of the reaction, but in order to raise the decomposition rate of the hydroperoxide, a long period of time for the reaction is required or the amount of the iron salt used should be increased.

From the present situation like this, the present inventors found that the reaction rate can markedly be improved when both an iron salt and a copper salt are present under a particular condition, resulting in a marked reduction in the amount of the iron salt used as well as a remarkable increase in the yield of the aromatic carbonyl compound.

The amount of the iron salt which can be used is 0.001 to 1 mole, preferably 0.005 to 0.5 mole, per mole of the hydroperoxide group of the hydroperoxide, and the amount of the copper salt which can be used is 0.01 to 4 moles, preferably 0.05 to 3 moles, per mole of the iron salt.

When the amount of the iron salt used is less than 0.001 mole per mole of the hydroperoxide group, the reaction rate is slow, and because of side reactions, the formation of alcohols becomes remarkable, so that such amount is disadvantageous. When the amount is more than 1 mole, the reaction rate becomes fast, but because of side reactions, the formation of phenols or heavy substances becomes remarkable, so that such amount is not advantageous. When the amount of the copper salt used is less than 0.01 mole per mole of the iron salt, there is no coexisting effect of the salt and, hence, no improvement in the yield of the aromatic carbonyl compounds is observed. When the amount is more than 4 moles, an improvement in the yield is observable to some degree, but the cost of catalyst in the production of the aromatic carbonyl compounds becomes high, so that such amount is finally disadvantageous and undesirable.

Further characteristics of the method of the present invention are that a ferrous salt and/or a ferric salt is used as the iron salt, and that a cuprous salt and/or a cupric salt is used as the copper salt.

Hitherto, ferrous salts alone have been used, but the present inventors found that the aromatic carbonyl compounds can also be obtained in good yields with ferric salts if a copper salt coexists.

Suitable examples of the iron salt which can be used in the present invention include iron sulfate, iron chloride, iron nitrate, iron citrate, iron lactate, iron oxalate, iron oxide (e.g., $Fe_2O_3$), iron hydroxide [e.g., $Fe(OH)_3$] and the like.

Suitable examples of the copper salt which can be used in the present invention include copper sulfate, copper chloride, copper nitrate, copper acetate, copper oxide (e.g., CuO), copper hydroxide [e.g., $Cu(OH)_2$] and the like. Most preferably, a combination of ferrous sulfate and/or ferric sulfate as the iron salt with copper sulfate as the copper salt is used.

An acid has an effect to inhibit the formation of sludge, and a mineral acid such as, for example, sulfuric acid, hydrochloric acid, nitric acid, etc., is preferably used, with the sulfuric acid being most preferably used.

In the present invention, the hydroperoxide can be used for the reaction as it is, but in order to allow the reaction to proceed smoothly, it is more preferred to use the hydroperoxide in the form of an appropriate organic solvent layer containing the hydroperoxide. Suitable examples of the organic solvent which can be used include benzene, toluene, xylene, methyl isobutyl ketone, or the compound represented by the formula (C)-1 or (C)-2.

The mixing ratio of the hydroperoxide-containing organic layer to the aqueous layer containing the iron salt, copper salt and acid is adjusted so that the aqueous layer is not less than 10 parts, preferably not less than 20 parts, per 100 parts by weight of the organic layer.

When the proportion of the aqueous layer is less than 10 parts, the reaction rate becomes slow, and because of side reactions, the formation of phenols or heavy substances becomes remarkable, so that such proportion is not desirable.

Further, in the present invention, the aqueous layer containing the iron salt, copper salt and acid can be reused after completion of the reaction by oily layer/aqueous layer separation. This is one of the characteristics markedly different from the prior art method with ferrous salts alone.

The reaction temperature is selected from a range of generally 30° to 100° C., preferably 40° to 90° C. When the reaction temperature is less than 30° C., the reaction rate is slow, and when it exceeds 100° C., side reactions increase, either of the both being undesirable.

The reaction is generally carried out under atmospheric pressure, but it can also be carried out under reduced pressure. The reaction can be carried out in any of batchwise and continuous systems.

After completion of the reaction, the compound represented by the formula (B)-1 or (B)-2 precipitates as a solid from the reaction mixture, or is recovered as an oily layer after the oily layer/aqueous layer separation. When a higher purity is required, it can be obtained by purification by the usual methods such as recrystallization, distillation or the like. When the organic solvent is used for the reaction, the compound can be recovered by separating the oily layer from the aqueous layer, removing the organic solvent by the usual methods such as distillation, and then distilling the bottom fraction under reduced pressure.

Furthermore, among the compounds represented by the formula (B)-1, m-(2-hydroxy-2-propyl)acetophenone and m-isopropenylacetophenone are a novel acetophenone. Though it is possible to produce m-isopropenylacetophenone directly from the hydroperoxide, it is industrially advantageous to produce m-isopropenylacetophenone by dehydrating m-(2-hydroxy-2-propyl)acetophenone in the presence of an acid catalyst because it can be produced in a high yield.

In the production of m-isopropenylacetophenone represented by the formula:

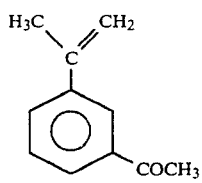

by dehydrating m-(2-hydroxy-2-propyl)acetophenone represented by the formula:

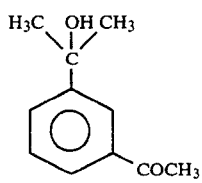

a decomposition reaction solution of m-(2-hydroxy-2-propyl)cumene hydroperoxide represented by the formula:

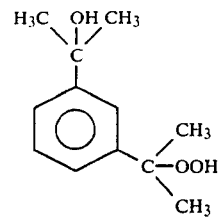

can be used. Further, when an organic solvent is used in the above decomposition reaction, a bottom fraction from which the organic solvent in the oily layer has been removed, a crude product of m-(2-hydroxy-2-propyl)-acetophenone, or a recrystallized product thereof can also be used.

Suitable examples of the acid catalyst which can be used include mineral acids, organic acids, solid acids and the like, specifically sulfuric acid, hydrochloric acid, p-toluenesulfonic acid, a strongly acidic ion exchange resin, silica-alumina, activated alumina, or mixtures thereof. The amount of the acid catalyst used varies depending upon the system of dehydration, but it is generally 0.0005 to 300 wt%, preferably 0.001 to 200 wt%, per the weight of m-(2-hydroxy-2-propyl)acetophenone. When the amount is less than 0.0005 wt%, the reaction rate is slow, and when it exceeds 300 wt%, degradation of m-isopropenylacetophenone formed becomes remarkable, either of the both being undesirable. The reaction temperature is generally 0° to 350° C., preferably 50° to 280° C. The reaction is generally carried out under atmospheric pressure, but it can be carried out by means of distillation under reduced pressure. Further, it is possible to carry out the dehydration in a gaseous phase under reduced pressure. The thus-formed m-isopropenylacetophenone can be easily separated and recovered from the reaction mixture by distillation. The dehydration can be carried out in any of batchwise and continuous system.

The present invention will be illustrated in detail with reference to the following examples, which are not, however, to be interpreted as limiting the invention thereto.

EXAMPLE 1

Into a 5-liter separable flask was charged 1,000 g of a methyl isobutyl ketone solution containing 19.9 wt% of m-(2-hydroxy-2-propyl)cumene hydroperoxide (containing 1.32 moles of a hydroperoxide group), and the temperature was raised to 80° C. while passing a nitrogen gas stream. After the temperature of the contents of the flask reached 80° C., 1,000 g of an aqueous solution containing 18.3 g of a ferrous sulfate hydrate (containing 0.066 mole of $Fe^{++}$), 10.5 g of copper sulfate (containing 0.066 mole of $Cu^{++}$) and 3.3 g of concentrated sulfuric acid was added thereto from a dropping funnel, and the reaction was carried out at 80° C. After 3 hours' reaction, it was found that the concentration of the remaining hydroperoxide was not more than 0.1 wt%, and hence, the reaction was substantially completed. The gas chromatographic analysis (hereafter GC analysis) showed that the yield of m-(2-hydroxy-2-propyl)acetophenone was 92%.

EXAMPLES 2 TO 6

Using a methyl isobutyl ketone solution of m-(2-hydroxy-2-propyl)cumene hydroperoxide, the reaction was carried out in the same manner as in Example 1 except that the amount of ferrous sulfate per mole of a hydroperoxide group and that of copper sulfate per mole of ferrous sulfate were varied as shown in Table 1. The results are also shown in Table 1.

TABLE 1

| Example No. | $Fe^{++}$/Hydroperoxide Group[1] | $Cu^{++}/Fe^{++}$ [2] | Reaction Time[3] (hr) | Yield[4] (%) |
|---|---|---|---|---|
| 2 | 0.05 | 0.1 | 6 | 88 |
| 3 | 0.05 | 0.5 | 4 | 90 |
| 4 | 0.05 | 2.0 | 3 | 93 |
| 5 | 0.1 | 0.1 | 3 | 88 |
| 6 | 0.1 | 1.0 | 1.5 | 91 |

Note:
Either reaction was carried out while passing a nitrogen gas stream.
[1] The number of moles of ferrous sulfate per mole of a hydroperoxide group.
[2] The number of moles of copper sulfate per mole of ferrous sulfate.
[3] A period of time which has passed until the concentration of the remaining hydroperoxide reaches 0.1 wt % or les.
[4] Yield of m-(2-hydroxy-2-propyl)acetophenone

COMPARATIVE EXAMPLE 1

Into a 5-liter separable flask was charged 1,000 g of a methyl isobutyl ketone solution containing 19.9 wt% of m-(2-hydroxy-2-propyl)cumene hydroperoxide (containing 1.32 moles of a hydroperoxide group), and the temperature was raised to 80° C. while passing a nitrogen gas stream.

After the temperature of the contents of the flask reached 80° C., 1,000 g of an aqueous ferrous sulfate solution containing 183 g of a ferrous sulfate hydrate (containing 0.66 mole of $Fe^{++}$) and 33 g of concentrated sulfuric acid was added thereto from a dropping funnel, and the reaction was carried out at 80° C. After 9 hours' reaction, it was found that the concentration of the remaining hydroperoxide was not more than 0.1 wt%.

The GC analysis showed that the yield of m-(2-hydroxy-2-propyl)acetophenone was 68%.

COMPARATIVE EXAMPLE 2

Into a 5-liter separable flask were charged 1,000 g of a methyl isobutyl ketone solution containing 19.9 wt% of m-(2-hydroxy-2-propyl)cumene hydroperoxide and 1,000 g of an aqueous layer containing 93 g of a ferric sulfate hydrate (containing 0.33 mole of $Fe^{+++}$), and the temperature was raised to 80° C. while passing a nitrogen gas stream. The reaction was carried out at 80° C. for 9 hours, but it was found that a considerable amount of the hydroperoxide remained undecomposed, and hence, the reaction did not take place substantially.

EXAMPLE 7

The reaction was carried out in the same manner as in Example 1 except that 18.5 g of a ferric sulfate hydrate (containing 0.066 mole of $Fe^{+++}$) was used in place of the ferrous sulfate hydrate. When the ferric sulfate was used, the decomposition rate of the hydroperoxide was somewhat slower than with the ferrous sulfate, but the concentration of the remaining hydroperoxide was not more than 0.1 wt% after 4.5 hours' reaction. The yield of m-(2-hydroxy-2-propyl)acetophenone was 87%.

EXAMPLE 8

The reaction was carried out in the same manner as in Example 1 except that the weight of the aqueous layer was made 500 g by decreasing the amount of water so that the weight ratio of the methyl isobutyl ketone solution of hydroperoxide to the aqueous layer containing ferrous sulfate, copper sulfate and the acid was 2:1. After 3.5 hours' reaction, the concentration of the remaining hydroperoxide was not more than 0.1 wt%.

The yield of m-(2-hydroxy-2-propyl)acetophenone was 86%.

EXAMPLES 9 TO 15

The reaction was carried out in the same manner as in Example 1 except that various hydroperoxides as shown in Table 2 were used in place of m-(2-hydroxy-2-propyl)cumene hydroperoxide. The reaction conditions and the results obtained are also shown in Table 2.

TABLE 2

| Example No. | Hydroperoxide | Reaction Conditions Temperature (°C.) | Time (hr) | Ferrous Sulfate (g) | Copper Sulfate (g) | Yield (%) | Remark (name of a product) |
|---|---|---|---|---|---|---|---|
| 9 | Cumene hydroperoxide | 80 | 3 | 19.2 | 11.0 | 92 | Acetophenone |
| 10 | Cymene hydroperoxide | 80 | 3 | 18.4 | 10.6 | 90 | Methylacetophenone |
| 11 | Ethylbenzene hydroperoxide | 80 | 2 | 21.1 | 12.1 | 94 | Acetophenone |
| 12 | m-Diisopropylbenzene dihydroperoxide | 80 | 3.5 | 24.6 | 14.1 | 85 | m-Diacetylbenzene |
| 13 | 1,3,5-Triisopropylbenzene trihydroperoxide | 80 | 4 | 27.8 | 15.9 | 78 | 1,3,5-Triacetylbenzene |
| 14 | Methyl cuminate hydroperoxide | 80 | 3 | 13.2 | 7.6 | 91 | Methyl acetylbenzoate |
| 15 | β-Isopropylnaphthalene hydroperoxide | 80 | 3 | 13.7 | 7.9 | 90 | β-Acetylnaphthalene |

Note:
[1] The hydroperoxides were used as a 20 wt % solution in the solvents described below, and the amount of the solution used was 1,000 g: Cumene for Example 9; cymene for Example 10; ethylbenzene for Example 11; methyl isobutyl ketone for Example 12; triisopropylbenzene for Example 13; and methyl isobutyl ketone for Examples 14 and 15.
[2] The aqueous layer was an aqueous solution containing ferrous sulfate, copper sulfate and concentrated sulfuric acid of 0.5 mole per mole of ferrous sulfate, and its amount was 1,000 g.

EXAMPLE 16

Recycled use of the aqueous layer recovered in Example 1 was carried out as follows: Procedure was carried out in the same manner as in Example 1; 1,000 g of a fresh methyl isobutyl ketone solution containing m-(2-hydroxy-2-propyl)cumene hydroperoxide which is a starting material was used for every recycled use; to the recovered aqueous layer were added, for every recycled use, a fresh ferrous sulfate hydrate of one-fifth of the amount in Example 1 and a fresh copper sulfate of one-tenth of the same; and the reaction time was made 3 hours so that the concentration of the remaining hydroperoxide was not more than 0.1 wt%. The results of five recycled experiments showed that the yield of m-(2-hydroxy-2-propyl)acetophenone was not less than 90% for every recycled use, and hence, the recycled use of the aqueous layer was possible.

EXAMPLE 17

Using as a starting material m-(2-hydroxy-2-propyl)acetophenone obtained in Example 1, m-isopropenylacetophenone was produced as follows.

To 50 g of m-(2-hydroxy-2-propyl)acetophenone was added as an acid 50 mg of p-toluenesulfonic acid, and the mixture was subjected to dehydration at atmospheric pressure at 180° C. for one hour and then distilled under 10 mm Hg. Thus, 36 g of a transparent fraction having a boiling point of 121° C./10 mm Hg was obtained.

As the results of NMR spectral analysis and mass spectral analysis, it was confirmed that the thus-obtained transparent fraction was m-isopropenylacetophenone (purity: 99.1%).

EXAMPLE 18

The same reaction as in Example 1 was carried out to obtain a bottom fraction, after distilling off methyl isobutyl ketone, containing 67 wt% of m-(2-hydroxy-2-propyl)acetophenone. Using as a starting material the thus-obtained bottom fraction, the same m-isopropenylacetophenone as in Example 17 was produced as follows.

To 150 g of the bottom fraction was added as an acid 0.15 g of p-toluenesulfonic acid (0.15% against m-(2-hydroxy-2-propyl)acetophenone), and the mixture was subjected to dehydration at atmospheric pressure at 190° C. for one hour and then distilled under 10 mm Hg. Thus, 88 g of a transparent fraction having a boiling point of 120°–122° C./10 mm Hg was obtained.

As the results of NMR spectral analysis and mass spectral analysis, it was confirmed that the thus-obtained transparent fraction was m-isopropenylacetophenone (purity: 97.5%).

While the invention has been described in detail and with reference to specific embodiments thereof, it will be apparent to one skilled in the art that various changes and modifications can be made therein without departing from the spirit and scope thereof.

What is claimed is:

1. A method for producing an aromatic carbonyl compound represented by the formula (B)-1 or (B)-2:

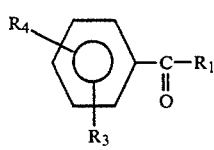
(B)-1 wherein $R_1$ is a hydrogen atom or a methyl group; and $R_3$ and $R_4$ are each a hydrogen atom, a $(C_1–C_3)$alkyl group,

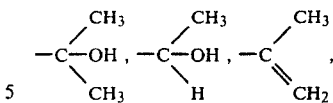

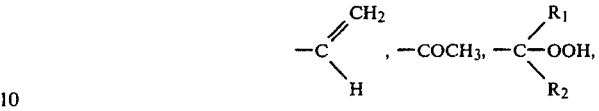

—COOH, or a carboxylic acid ester group,

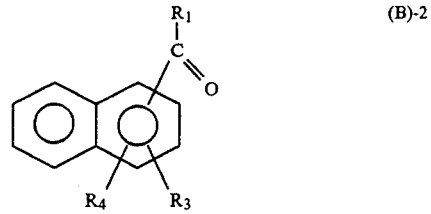
(B)-2 wherein $R_1$, $R_3$ and $R_4$ are the same as defined above, comprising decomposing a hydroperoxide represented by the formula (A)-1 or (A)-2:

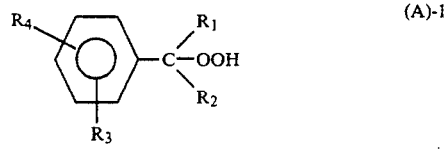
(A)-1 wherein $R_2$ is a hydrogen atom or a methyl group; and $R_1$, $R_3$ and $R_4$ are the same as defined above.

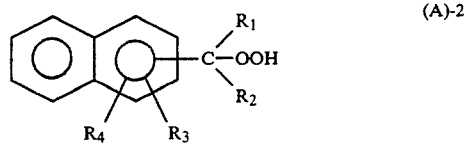
(A)-2 wherein $R_1$, $R_2$, $R_3$ and $R_4$ are the same as defined above, in an inert gas atmosphere in the presence of an aqueous layer containing an iron salt, a copper salt and an acid.

2. A method as claimed in claim 1, wherein said iron salt and copper salt are a water-soluble salt thereof.

3. A method as claimed in claim 1, wherein the amount of said iron salt is 0.001 to 1 mole per mole of the hydroperoxide group of said hydroperoxide, and the amount of said copper salt is 0.01 to 4 moles per mole of said iron salt.

4. A method as claimed in claim 2, wherein said iron salt and copper salt are a sulfate thereof.

5. A method as claimed in claim 1, wherein said hydroperoxide is used as a solution in an organic solvent.

6. A method as claimed in claim 5, wherein the weight of said aqueous layer containing said iron salt, copper salt and acid is not less than 10 parts per 100 parts by weight of the organic solvent layer containing said hydroperoxide.

* * * * *